(12) United States Patent
Yahav

(10) Patent No.: US 9,387,027 B2
(45) Date of Patent: Jul. 12, 2016

(54) IMPLANTABLE FIXTURE

(71) Applicant: Jonathon Yigal Yahav, Skokie, IL (US)

(72) Inventor: Jonathon Yigal Yahav, Skokie, IL (US)

( * ) Notice: Subject to any disclaimer, the term of this patent is extended or adjusted under 35 U.S.C. 154(b) by 212 days.

(21) Appl. No.: 13/742,654

(22) Filed: Jan. 16, 2013

(65) Prior Publication Data

US 2014/0200620 A1 Jul. 17, 2014

Related U.S. Application Data

(60) Provisional application No. 61/737,060, filed on Dec. 13, 2012.

(51) Int. Cl.
*A61B 17/86* (2006.01)
*A61C 8/00* (2006.01)

(52) U.S. Cl.
CPC .............. *A61B 17/863* (2013.01); *A61C 8/006* (2013.01); *A61C 8/0018* (2013.01); *A61C 8/0022* (2013.01); *A61C 8/0068* (2013.01); *A61B 17/8635* (2013.01)

(58) Field of Classification Search
CPC ........... A61B 2017/8655; A61B 17/84; A61B 17/86–17/8645; A61B 2017/867–2017/868; F16B 25/0057; F16B 25/0042; A61C 8/0022; A61C 8/0024; A61C 8/0025
USPC .......... 606/300, 301–321, 323; 433/173, 174; 411/411, 412, 423, 420; 623/16.11
See application file for complete search history.

(56) References Cited

U.S. PATENT DOCUMENTS

| | | | |
|---|---|---|---|
| 5,078,607 A | 1/1992 | Niznick | |
| 5,199,873 A | 4/1993 | Schulte et al. | |
| 5,259,398 A * | 11/1993 | Vrespa | 128/898 |
| 5,269,685 A | 12/1993 | Jorneus et al. | |
| 5,733,124 A * | 3/1998 | Kwan | 433/173 |
| 5,759,035 A * | 6/1998 | Ricci | 433/174 |
| 5,816,812 A | 10/1998 | Kownacki et al. | |
| 6,099,312 A * | 8/2000 | Alvaro | 433/174 |
| 6,273,721 B1 * | 8/2001 | Valen | 433/174 |
| 6,315,564 B1 * | 11/2001 | Levisman | 433/174 |
| 6,610,099 B1 * | 8/2003 | Albrektsson et al. | 623/23.15 |
| 6,979,163 B2 * | 12/2005 | Brletich et al. | 411/418 |
| 2003/0082026 A1 * | 5/2003 | Brletich et al. | 411/311 |
| 2005/0147943 A1 * | 7/2005 | Chang | 433/174 |
| 2005/0152770 A1 * | 7/2005 | Tschakaloff et al. | 411/403 |
| 2006/0147880 A1 * | 7/2006 | Krumsiek et al. | 433/174 |
| 2006/0241623 A1 * | 10/2006 | Lim et al. | 606/73 |
| 2007/0148622 A1 * | 6/2007 | Gogarnoiu | 433/173 |
| 2008/0160483 A1 * | 7/2008 | Danger et al. | 433/174 |
| 2008/0254411 A1 * | 10/2008 | Bondar | 433/174 |
| 2008/0280254 A1 * | 11/2008 | Ackermann | 433/174 |

(Continued)

*Primary Examiner* — Matthew Lawson
*Assistant Examiner* — Amy Sipp
(74) *Attorney, Agent, or Firm* — Law Offices of Steven W. Weinrieb

(57) ABSTRACT

A self-tapping fixture is implantable in a bone. The fixture extends generally longitudinally from an apical end to a distal end along a longitudinal axis L and has a periphery, the periphery comprises a first zone A extending away from the apical end to merge with a second zone B, the second zone B extending away from the first zone A to merge with a third zone C, the third zone C extending away from the second zone B to merge with a fourth zone D and the fourth zone D extending away from the third zone to terminate at the distal end of the fixture, and the third zone C is provided with a plurality of thread wraps each merging from the periphery and extending generally radially away therefrom to terminate at a generally rounded wrap ends.

6 Claims, 2 Drawing Sheets

(56) References Cited

U.S. PATENT DOCUMENTS

| | | |
|---|---|---|
| 2009/0298015 A1* | 12/2009 | Al-Attar ............... 433/174 |
| 2010/0112520 A1* | 5/2010 | Worthington ............... 433/169 |
| 2010/0112523 A1* | 5/2010 | Fromovich et al. ............... 433/174 |
| 2010/0248187 A1* | 9/2010 | Naert et al. ............... 433/174 |
| 2010/0261141 A1* | 10/2010 | Ajlouni et al. ............... 433/174 |
| 2011/0020769 A1* | 1/2011 | Yun ............... 433/174 |
| 2011/0117522 A1* | 5/2011 | Verma et al. ............... 433/174 |
| 2012/0178048 A1* | 7/2012 | Cottrell ............... 433/174 |
| 2012/0237898 A1* | 9/2012 | Palti et al. ............... 433/174 |

\* cited by examiner

IMPLANTABLE FIXTURE

IMPLANTABLE FIXTURE

IMPLANTABLE FIXTURE

CROSS-REFERENCE TO RELATED APPLICATION

This patent application is a non-provisional conversion patent application of U.S. Provisional Patent Application Ser. No. 61/737,060 filed on Dec. 13, 2012, the priority benefits of which are hereby claimed.

FIELD OF THE INVENTION

The present invention relates generally to implanted fixtures designed to be implanted in a bone.

BACKGROUND OF THE INVENTION

Examples and limitations related therewith brought herein below are intended to be illustrative and not exclusive. Other limitations of the related art will become apparent to those of skill in the art upon a reading of the specification and a study of the figures. An illustrative example of an implantable fixture is shown in the drawings. The fixture is preferably made of a biomechanical material such as, but not limited to, titanium or a titanium alloy. This fixture is designed to be implanted in bone of a patient and becomes the base, or root, for an addendum to be mounted thereon.

U.S. Pat. No. 5,078,607 to Gerald A. Nimick discloses, inter Alia, "A dental implant anchor includes a body portion having a first external wall portion carrying one or more circumferential projections separated by circumferential grooves and, below, a second external wall portion carrying threads. The implant can include a head portion with a smooth external wall; a through-hole and an apical hole passing through the bottom of the implant; and internal structure for engaging a tool for inserting the implant in a passage formed in bone tissue. This internal structure can be in a top portion, or in an internal passage in the body portion of the implant."

U.S. Pat. No. 5,269,685 to Jorneus, Frillesas and Anders Boss, discloses, inter Alia, "A screw-shaped titanium anchoring member for permanent anchorage in bone tissue, specifically permanent anchorage of artificial teeth or tooth bridges in the jaw-bone, comprises at east one cavity located at the forward tip of the screw, the edges of the at least one cavity on the outer threaded cylindrical surface forming cutting tooth with cutting edge to provide self-tapping when the anchoring member is screwed into a bored hole in the bone tissue and the total volume of the at least one cavity being adapted to contain the scraped off bone tissue material. The anchoring member on the outer cylindrical surface of the cutting tooth, a short distance behind its cutting edge, is provided with a clearance surface defined on the outer surface of the anchoring member, which when seen in a cross-section through the cutting part of the anchoring member, is slightly beveled a short distance behind the threaded cutting edge."

U.S. Pat. No. 5,199,873 to Willi Schulte, Freimut Vizethum, Walter Hund Willi Schulte, Freimut Vizethum, and Walter Hund, discloses, inter Alia, "A dental implant including a post which can be anchored in the jawbone of a dental patient and a replacement tooth head fastenable to said post. The post has at its crown end a recess for mounting a replacement tooth. The outside surface of the post is stepped down in at least two, and preferably three or four, steps to an apical root end opposite said crown end. At least one of the steps carries an external screw thread, and of two adjacent steps, the step closer to the apical root end has a thread crest diameter which is not larger than the base diameter of the adjacent step situated closer to the crown end of the implant."

U.S. Pat. No. 5,816,812 to Charles D. Kownacki, Wade W. Prescott, and Rick A. Buss, discloses, inter Alia, "A self-tapping dental prosthetic implant has a blunt leading end, a tapered first section which has a uniform minor diameter and a uniformly increasing major diameter, a second section having uniform minor and major thread diameters, a third section with a uniform major thread diameter and a outwardly tapering minor diameter and fourth section which has a diameter larger than any other segment and a relatively low profile (that is, short axial length). A thread-cutting groove extends over a substantial portion of the threaded length of the implant. A stepped drill with a tip having a large included angle is used to drill a pilot hole permitting anchoring in the proximate and distal portions of cortical bone by the threaded implant."

In some other implant fixture designs, specifically other self-tapping versions, a hole is bored into the bone at a diameter approximating the minor or base diameter of the thread. The top portion of the hole is counterbored or otherwise pre-enlarged to the major diameter of the implant fixture so that a relatively wide unthreaded portion of the implant can be placed into the enlarged hole with a precise fit in order to prevent any bacterial leakage (known as micro-leakage) into the surgical site. The fit between the implant fixture and hole is very important to the healing of and integration of the implant fixture into the bone tissue. This procedure, although somewhat effective, does not take advantage of the hard cortical bone layer that surrounds the perimeter of the mandible and maxilla as a medium in which to anchor.

Various other features, advantages and characteristics of the present invention will become apparent after a reading of the following detailed description thereof.

Thus, it may be advantageous to have a fixture that may offer enhanced osseointegration as well as better initial stability. Numerous other advantages and features of the present invention may become readily apparent from the following detailed description of the invention and the embodiment thereof, from the claims and from the accompanying drawings.

SUMMARY OF THE INVENTION

In the following disclosure, aspects thereof are described and illustrated in conjunction with systems and methods which are meant to be exemplary and illustrative, not limiting in scope. The present disclosure may be further directed to a method of utilization and/or usage of such apparatuses.

Accordingly, it is an object of the present invention to provide a novel implantable bone fixture designed to enhance the safety of the surgical steps for the successful bone integrity at the completion of the implant and its immediate stability. Another object of the present invention is to provide a novel implantable bone fixture which may assist in providing long-term stress stability and distribution and absorbing of acute forces.

In an illustrative, exemplary and/or non-limiting embodiment of the present invention, the implant fixture extends generally longitudinally from an apical end to a distal end along a longitudinal axis L and has an outer periphery. The outer periphery comprises four zones: a first zone A extends away from the apical end so as to merge with a second zone B; the second zone B extends away from the first zone A so as to merge with a third zone C; the third zone C extends away from the second zone B so as to merge with a fourth zone D; and the fourth zone D extends away from the third zone C so as to terminate at the distal end of the fixture. The third zone C is provided with a plurality of thread wraps, each thread wrap merges from the periphery and extends generally radially away therefrom so as to terminate at generally rounded wrap ends.

Potentially, the third zone C is provided with at least one tub having a generally rectangular, flat floor.

Further potentially, the floor extends laterally between two parallel longs and has a longitudinal tub axis T extending therebetween and generally parallel thereto.

Moreover, the tub axis T is tilted relative to the longitudinal axis L by a tilt angle ι.

Possibly, the first zone A is provided with a plurality of first zone thread wraps each merging with the periphery and extending generally radially away therefrom to terminate at a generally sharp first wrap ends.

Further possibly, the second zone B is provided with a plurality of second zone thread wraps each merging with the periphery and extending generally radially away therefrom to terminate at a generally blunt second wrap ends.

Optionally, the fixture is generally of a round-nose ogive-shape.

Generally, the first zone A is an entry zone, the second zone B is a penetration and expansion zone, the third zone C is a stretching and securing zone, and the fourth zone D is a stabilizing zone.

In addition to the exemplary aspects and embodiments described or noted hereinabove, further aspects and embodiments will become apparent by reference to the figures and by study of the following detailed description.

BRIEF DESCRIPTION OF THE DRAWINGS

Exemplary and/or illustrative embodiments of the present invention will be presented herein below in the following figures, by way of example only. The present invention may be best understood from the following detailed description when read in connection with the accompanying drawings. In the drawings, like segments have the same reference numerals. When pluralities of similar segments are present, a single reference numeral may be assigned to each plurality of similar segments with a small letter designation referring to specific segments. When referring to the segments collectively or to a non-specific one or more of the segments, the small letter designation may be dropped. It should be emphasized that according to common practice, various features of the drawings are not drawn to scale unless otherwise indicated. On the contrary, dimensions of various features may be expanded and/or reduced and/or roughly shown and/or omitted entirely, to show details of particular components, for the purpose that the present disclosure may be more fully understood from the detailed description and the accompanying schematic figures.

Reference will now be made to the accompanying drawings, in which.

DETAILED DESCRIPTION OF THE INVENTION

As required, a schematic, exemplary embodiment of the present fixture is disclosed herein, however, it is to be understood that the disclosed embodiment is merely exemplary of the present disclosure, which may be embodied in various and/or alternative forms. Specific structural and functional details disclosed herein are not to be interpreted as limiting, but merely as a basis for the claims, and as a representative basis for teaching one skilled in the art to variously employ the present disclosure in virtually any appropriately detailed structure.

Aspects, advantages and/or other features of the exemplary embodiment of the disclosure will become apparent in view of the following detailed description, which discloses various non-limiting embodiments of the invention. In describing exemplary embodiments, specific terminology is employed for the sake of clarity. However, the embodiments are not intended to be limited to this specific terminology. It is to be understood that each specific segment includes all technical equivalents that operate in a similar manner to accomplish a similar purpose.

Exemplary embodiments may be adapted for many different purposes and are not intended to be limited to the specific exemplary purposes set forth herein. Other non-limiting examples of such embodiments are compositions that may be used, for example, for structural components. Those skilled in the art would be able to adapt the embodiments of the present disclosure, depending, for example, upon the intended use of the embodiment.

Figure 1:
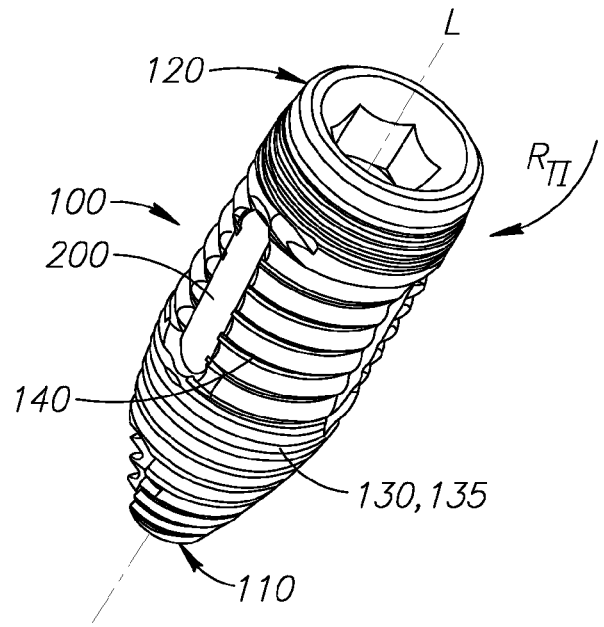
FIG. 1 is a schematic general perspective representation of an exemplary implantable fixture constructed in accordance with the principles and teachings of the present invention.
Figure 2:
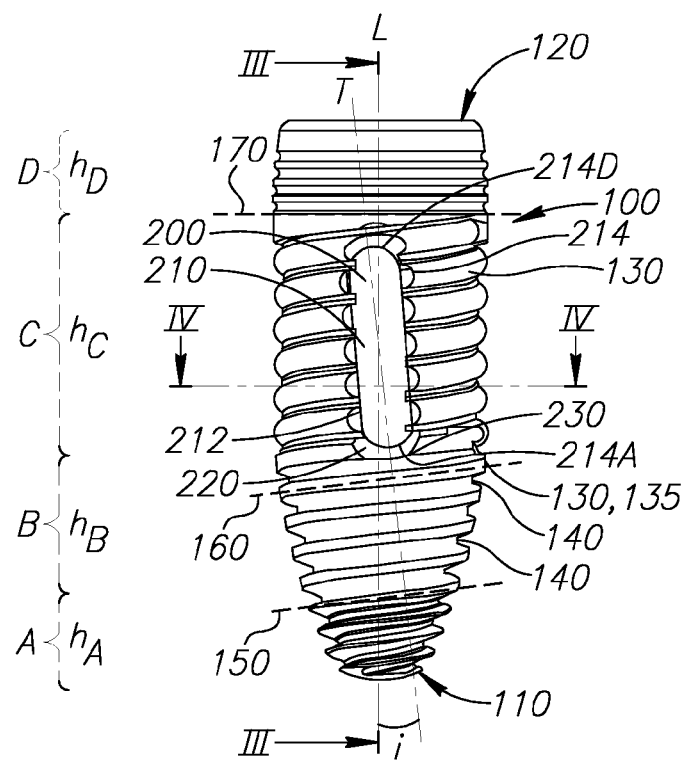
FIG. 2 is an elevational view of the implantable fixture of FIG. 1.

An embodiment of the self-tapping implantable fixture of the present invention is depicted in FIGS. 1 and 2, generally as 100. The fixture 100 is generally of a round-nose bullet shape or rounded ogive, extends generally longitudinally away from an apical end 110 (as can be seen adjacent the bottom left position on FIG. 1) so as to terminate at a distal end 120 (as can be seen adjacent the top right position on FIG. 1) along a longitudinal axis L. An external periphery 140 of the fixture 100 generally defines four longitudinally consecutive zones: a first zone A, a second zone B, a third zone C and a fourth zone D, with zone A being disposed adjacent the apical end 110 of the fixture 100, and with zone D being disposed adjacent the distal end 120 of the fixture 100 as may best be seen in FIG. 2.

The first zone A comprises an entry zone of the fixture 100, extending generally distally away from the apical end 110 of the fixture 100 to a first transition 150 having a first height $h_A$; the second zone B is a penetrating and stretching zone, extending generally distally away from the first transition 150 to a second transition 160 and having a second height $h_B$; the third zone C is a stretching and securing zone, extending generally distally away from the second transition 160 to a third transition 170 and having a third height $h_C$; and the fourth zone D is a stabilizing zone, extending generally distally away from the third transition 170, so as to terminate at the distal end 120, and has a fourth height $h_D$.

The external periphery 140 is formed with an external thread 130 having at least one thread wrap 135 projecting generally radially outwardly away from the external periphery 140 while spiraling thereabout from the apical end 110, through the first zone A to the third zone C, for advancing and anchoring the fixture 100 into an appropriate portion of a patient's bone. The fourth zone D comprises a plurality of circumferentially-extending, generally parallel, alternating ridges and troughs, designed to assist the fixture to retain its position within a bone, particularly in a stiff and dense portion of a bone. While the present disclosure discusses and shows a thread having a single starting thread, two and/or three starting threads may be employed without limiting the scope of the present disclosure.

Figure 3:
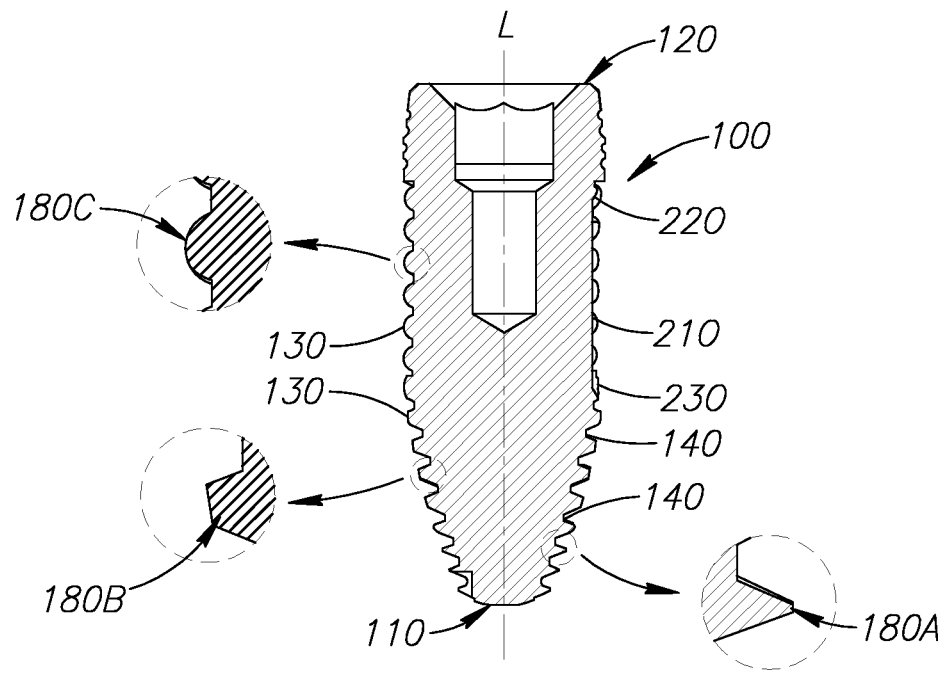
FIG. 3 is a schematic general longitudinal cross-sectional view of the implantable fixture of FIG. 1 taken along the line III-III in FIG. 2.

Each thread wrap 135 merges with the external periphery 140 and extends generally radially outwardly away therefrom so as to terminate at a thread wrap end or crest portion 180. As may best be seen in FIG. 3, each one of the thread wrap ends or crest portions within the first zone A, the second zone B, and the third zone C, is generally characterized by means of a different shape of the wrap end or crest portion 180. More particularly, each one of the wrap ends or crest portions of the first zone A has a generally sharp outwardly convex first wrap end or crest portion $180_A$, each one of the wrap ends or crest portions of the second zone B has a generally blunt inwardly concave second wrap end or crest portion $180_B$, and each one of the wrap ends or crest portions of the third zone C has a generally rounded inwardly concave third wrap end $180_C$.

Figure 4:
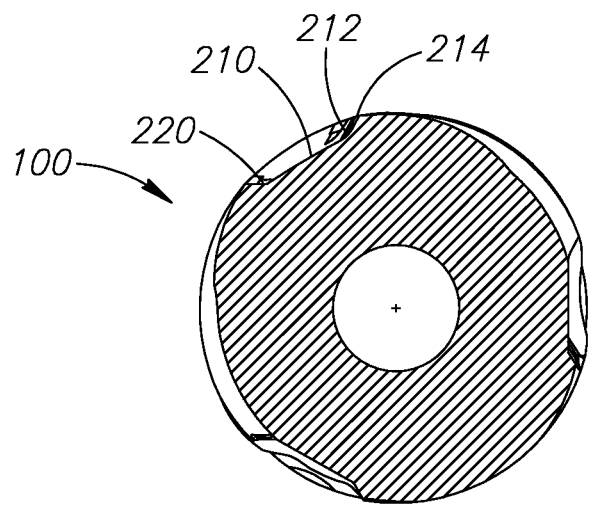
FIG. 4 is a schematic general lateral cross-sectional view of the implantable fixture of FIG. 1 taken along the line IV-IV in FIG. 2.

The third zone C is also provided with a plurality of circumferentially-spaced-apart tubs 200, as can best be seen in FIGS. 1, 2, and 4. Each tub 200 comprises a generally longitudinally-extending, generally rectangular, flat structure having rounded ends and a floor 210 extending laterally between two generally parallel long sides 212 with two opposing short sides 214 extending therebetween and meeting therewith, with a peripherally extending wall 220 extending upwardly and outwardly away therefrom so as to meet the external periphery 140 of the fixture 100 at a rim 230. A distal short $214_D$ is disposed towards the distal end 120 of the fixture 100, while an apical short $214_A$ is disposed towards the apical end 110 thereof. A longitudinal tub axis T extends between the two opposing short sides 214 between the two long sides 212 and generally parallel thereto. The tub 200 may be tilted relative to the fixture 100 so that the distal short $214_D$ may be disposed tangentially forwardly in a threading-in direction $R_{TT}$ relative to the apical short $214_A$ of each tub 200 while the tub axis T may be tilted relative to the longitudinal axis L by a tilt angle ι.

As the fixture 100 is implanted into an implant site (not shown), the first zone A enters a bore (not shown) created within the implant site (not shown). The threads formed upon the first zone A with their sharp first wrap ends or crest portions $180_A$ dig into the walls of the bore (not shown). As the fixture is further threaded into the bore (not shown), the threads within the second zone B cut and displace the walls of the bore (not shown) generally radially outwardly. When the third zone C is submerged into the bore, the rounded wrap ends or crest portions $180_C$ urge the walls of the bore generally radially outwardly still further than what was achieved by the second zone B (because of the generally ogive-shape of the fixture 100), while the plurality of the circumferentially-spaced-apart tubs 200 locally relieve pressure by allowing the walls of the bore (not shown) to expand thereto, thus securing the fixture and relieving pressure from the walls of the bore, thereby assisting in the healing and stabilization of the fixture 100 within the bore (not shown). The fourth zone D, comprising the plurality of circumferentially-extending, generally parallel, alternating ridges and troughs, leans against generally stiffer and denser cordial bone, so as to provide the implantable fixture 100 with its final stability and to thereby assist in retaining the implantable fixture 100 in its position.

Various changes, alternatives, and modifications to the specific embodiments discussed above will become apparent to one of ordinary skill in the art following a reading of the foregoing specification. It is intended that all such changes, alternatives, and modifications as come within the scope of the appended claims be considered part of the present invention.

Additionally, all numerical terms, such as, but not limited to, "first", "second", "third", or any other ordinary and/or numerical terms, should also be taken only as identifiers, to assist the reader's understanding of the various embodiments, variations and/or modifications of the present disclosure, and may not create any limitations, particularly as to the order, or preference, of any embodiment, variation and/or modification relative to, or over, another embodiment, variation and/or modification.

Similarly, adjectives such as, but not limited to, "articulated", "modified", or any adjectives similar thereto, should be construed broadly, and only as nominal, and may not create any limitations, not create any limitations, particularly as to the description, operation, or use unless specifically set forth in the claims.

In methodologies directly or indirectly set forth herein, various steps and operations are described in one possible order of operation, but those skilled in the art will recognize that steps and operations may be rearranged, replaced, or eliminated without necessarily departing from the spirit and scope of the present disclosure as set forth in the claims. It is intended that all matter contained in the above description or shown in the accompanying drawings shall be interpreted as illustrative only and not limiting. Changes in detail or structure may be made without departing from the spirit of the present disclosure as defined in the appended claims.

While certain exemplary embodiments have been described and shown in the accompanying drawings, it is to be understood that such embodiments are merely illustrative of and not restrictive on the broad present disclosure, and that this present disclosure not be limited to the specific constructions and arrangements shown and described, since various other modifications and/or adaptations may occur to those of ordinary skill in the art. It is to be understood that individual features shown or described for one embodiment may be combined with individual features shown or described for another embodiment. It is to be understood some features are shown or described to illustrate the use of the present disclosure in the context of functional segments and such features may be omitted within the scope of the present disclosure and without departing from the spirit of the present disclosure as defined in the appended claims.

The invention claimed is:

1. An implantable fixture for implantation within a bone site, comprising:
    a fixture extending generally longitudinally from an apical end to a distal end and defined around a central longitudinal axis L;
    a bore defined within said distal end of said fixture around an axis that is coincident with said central longitudinal axis L of said fixture;
    said fixture having an outer peripheral surface wherein said outer peripheral surface comprises a first zone A extending axially away from said apical end and toward said distal end so as to merge with a second zone B, said first zone A comprising a plurality of helical threads wherein crest portions thereof have substantially sharp triangular cross-sectional configurations so as to permit said helical threads of said first zone A to cut into and enter the bone site; said second zone B extending axially away from said first zone A and toward said distal end so as to merge with a third zone C, said second zone B comprising a plurality of helical threads wherein crest portions thereof have substantially blunt trapezoidal cross-sectional configurations so as to permit said helical threads of said second zone B to penetrate and enlarge the bone site; and said third zone C extending axially away from said second zone B and toward said distal end; said third zone C comprising a plurality of helical threads wherein crest portions thereof have substantially semi-circular cross-sectional configurations so as to permit said helical threads of said third zone C to advance and anchor said fixture within the bone site; and a plurality of tubs equiangularly spaced in a circumferential manner upon said outer peripheral surface of said fixture, each of said plurality of tubs having a longitudinal axis T which is tilted at a predetermined angle relative to said central longitudinal axis of said fixture, and each one of said plurality of tubs is wholly confined longitudinally within said third zone C so as to effectively relieve pressures generated at the bone site as a result of said fixture being implanted into the bone at the bone site.

2. The fixture of claim 1, wherein said plurality of tubs have a generally rectangular, flat floor.

3. The fixture of claim 2, wherein said floor extends laterally between two parallel long sides which extend generally parallel to said longitudinal tub axis T.

4. The fixture of claim 1, wherein said fixture has a substantially round-nose ogive configuration.

5. The fixture as set forth in claim 1, wherein:
said plurality of tubs comprises three tubs equiangularly disposed in a circumferential manner upon said outer peripheral surface of said fixture and around said longitudinal axis of said fixture.

6. The fixture as set forth in claim 1, wherein:
each one of said plurality of tubs has a substantially rectangular configuration comprising a pair of oppositely disposed parallel long sides, a pair of oppositely disposed ends, and a floor region.

* * * * *